United States Patent

Brattsev et al.

[11] Patent Number: 6,143,264
[45] Date of Patent: Nov. 7, 2000

[54] BORON COMPOUNDS

[75] Inventors: Victor Alexandrovich Brattsev, Moscow, Russian Federation; John Howell Morris, Helensburgh, United Kingdom

[73] Assignee: The University of Strathclyde, United Kingdom

[21] Appl. No.: 09/091,580

[22] PCT Filed: Dec. 17, 1996

[86] PCT No.: PCT/GB96/03115

§ 371 Date: Aug. 26, 1998

§ 102(e) Date: Aug. 26, 1998

[87] PCT Pub. No.: WO97/23487

PCT Pub. Date: Jul. 3, 1997

[30] Foreign Application Priority Data

Dec. 12, 1995 [GB] United Kingdom .................. 9526126

[51] Int. Cl.$^7$ ................................ C01B 6/15; C07F 5/02
[52] U.S. Cl. .................................. 423/286; 568/5; 568/6; 423/276; 423/278; 423/283
[58] Field of Search ...................... 568/4, 5, 6; 423/278, 423/276, 283, 286

[56] References Cited

U.S. PATENT DOCUMENTS 4,150,057  4/1979  Sayles .......................................... 568/5

OTHER PUBLICATIONS

CA:84:79701 abs of JP50092897, Dec. 1973.
CA:107:145255 abs of Acts Crystallorg Sect C: Cryst. Struct. Commun. by Nakai, H., C43(7) pp. 1420–2, 1987.
Chemistry of Boranes. XIX. Derivative Chemistry of $B_{10}H_{10}^{-2}$ and $B_{12}H_{12}^{-2}$, W. H. Knoth, Jr. et al., Chemistry of Boranes, Oct. 5, 1964, pp. 3973–3983.
Synthesis and Chemistry of Mercaptoundecahydro–closo–dodecaborate(2–); E. I. Tolpin et al., Inorganic Chemistry, vol. 17, No. 10, 1978, pp. 2867–2873.
Chemistry of Boranes. XX. Syntheses of Polyhedral Boranes, H. C. Miller et al., Inorganic Chemistry, vol. 3, No. 10, Oct. 1964, pp. 1456–1463.
Darstellung und Charakterisierung von Thiocyanatderivaten der Hydroboratanionen $B_{10}H_{10}^{2-}$ und $B_{12}H_{12}^{2-}$, H. G. Srebny et al., Z. anorg.allg.Chem. 513 (1984)7–14, pp. 7–14.
A Novel Synthesis of the $B_{12}H_{12}^{2-}$ Anion, N. N. Greenwood et al., Proceedings of the Chemical Society, Nov. 1963, p. 338.
Dodecahydrododecaborate (2–) anions. W. V. Hough et al., 49–Industrial Inorganics, vol. 85, 1976, pp. 126754.
Method of producing cesium mercaptoundeca=hydrododecaborate, V. A. Brattsev et al., 49–Industrial Organics, vol. 107, 1987, pp. 179482.
A convenient preparation of $^{10}$B–enriched $B_{12}H_{11}SH$::an agent for neutron capture therapy, M. Komura et al., 107:88504d 1987, Chemabstracts.
CA:107:179481 abs of SU1328290, May 1985.
CA:103:110670 abs of Polyhedron 4(7) pp 1329–31 by Power, 1985.
CA:102:178143 abs of Bull Soc Chim Fr (11–12 pt 1) pp 336–338 by Ouassas, 1984.
Chemiche Berichte, Inorganic and Organometallic Chemistry, vol. 129, 1996, pp. 1531–1534.
Chemical Abstracts, vol. 84, No. 12, Mar. 22, 1976, Columbus, Ohio, US; Abstract No. 79701, XP002029960.

Primary Examiner—Jean F Vollano
Attorney, Agent, or Firm—Alston & Bird LLP

[57] ABSTRACT

Process for the preparation of undecahydrododecaborate anions $[B_{12}H_{(12-n)}(XCN)_n]^{2-}$ or $[B_{12}H_{11}XH]^{2-}$ or a non-ahydrodecaborate anions $[B_{10}H_{(12-n)}(XCN)_n]^{2-}$ or $[B_{10}H_9XH]^{2-}$ or anions of formula $[B_{12}H_{11}SC(NR^1R^2)_2]^{-1}$ wherein X=O, S, or Se.

6 Claims, 3 Drawing Sheets

BORON COMPOUNDS

This application is a 371 of PCT/GB96/03115, filed Dec. 17, 1996 now WO97/23487.

FIELD OF THE INVENTION

The present invention relates to the preparation of boron compounds and in particular the production of substituted undecahydrododecaborate anions $[B_{12}H_{11}XH]^{2-}$ and $[B_{12}H_{(12-n)}(XCN)_n]^{2-}$, and nonahydrodecaborate anions $[B_{10}H_9XH]^{2-}$ and $[B_{10}H_{(10-n)}(XCN)_n]^{2-}$ where X and n are defined herein.

BACKGROUND

Boron compounds have been used for the treatment of cancer through $^{10}B$ neutron capture therapy (BNCT). Various derivatives of dodecahydrodecaborate $[B_{12}H_{12}]^{2-}$ and decahydrodecaborate $[B_{10}H_{10}]^{2-}$ have been synthesised. The sulphydryl-containing borane anion $[B_{12}H_{11}SH]^{2-}$ (BSH) has been found to be a most suitable species for the treatment of glioma by BNCT. It is found that BSH is preferentially taken up by the brain cancer tumour (glioma), which allows selective targeting of thermal or epithermal neutrons. Presently, there is no treatment for glioma and early death of the patient is to be expected.

The compound BSH has been known for some time and is approved for therapy in the USA. A number of syntheses of BSH have been reported in the literature (W. H. Knoth, J. C. Sauer, D. C. England, W. R. Hertler and E. L. Muetterties, J. Am. Chem. Soc., 1964, 86, 3973; E. I. Tolpin, G. R. Wellum and S. A. Berly, Inorg. Chem., 1978, 17, 2867; T. Nakagawa, T. Yoshizaki and K. Aono, J. P. Kokai 75 92897 C.A. 1976 84: 79701v; M. Komura, K. Aono, K. Nagasawa and S. Sumimoto, Chem. Express, 1987, 2, 173; V. A. Brattsev and O. R. Sagitullin Pat. USSR 1328290 (1987) C.A.; 1987, 107: 179481k). However, these synthetic methods are complicated and generally involve many synthetic steps. Certain of the intermediate products may be toxic, which leads to purification problems. Finally, the overall yields are generally poor. All syntheses start from the dodecahydrododecaborate anion $[B_{12}H_{12}]^{2-}$ which can be obtained in high yield when decaborane is treated with triethylamine-borane (N. N. Greenwood and J. H. Morris, Proc. Chem. Soc., 1963, 338.) $B_{10}H_{14}+2Et_3NBH_3 \rightarrow [Et_3NH]_2 [B_{12}H_{12}]+3H_2$.

Alternatively, it can be obtained by the reaction: $10BH_3SMe_2+2NaBH_4 \rightarrow Na_2[B_{12}H_{12}]+10SMe_2+13H_2$ (H. C. Miller, N. E. Miller and E. L. Muetterties, Inorg. Chem., 1964, 3, 1456; W. V. Hough, C. R. Guibert, and G. T. Hefferan, U.S. Pat. No. 3,961,017. C.A. 1976, 85, P126732V).

In the best reported synthesis (Komura et al., see above) seven steps are involved in converting this compound to $Na_2[B_{12}H_{11}SH]$. The overall yield is 68% though in practice this may represent a maximum rather than a routine achievable yield.

The syntheses of the $[B_{12}H_{11}SCN]^{2-}$ anion, as salts with the cations $[Et_3NH]^+$, $[Et_4N]^+$, $[(Ph_3P)_2N]^+$, $Na^+$, or $Cs^+$, are more efficient than earlier reported preparations (e.g. H. -G. Srebny and W. Preetz, Z. anorg. allg. Chem., 1984, 513, 7). Previously reported methods require the inconvenient prior preparation of $(SCN)_2$ from $Pb(SCN)_2$ and $Br_2$, and the use of $[Bu_4N]_2[B_{12}H_{12}]$ in $CH_2Cl_2$. The methods of the present invention conveniently start from simple thiocyanate salts, and easily synthesised salts of $[B_{12}H_{12}]^{2-}$ with the cations $[Et_3NH]^+$, $Na^+$, or $K^+$. The reactions may also be carried out in aqueous solutions and provide quantitative yields. The compound, as its sodium salt, has excellent potential for neutron capture therapy, in view of its low biological toxicity, and good tumour-localising properties in a tumour model system.

The synthesis of the 1,7-isomer (and the 1,12-isomer as a small byproduct) of salts of $[B_{12}H_{11}(SCN)_2]^{2-}$ have not been reported previously. Such compounds are also believed to have potential for neutron capture therapy.

SUMMARY OF THE INVENTION

It is an object of the present invention to mitigate these problems and provide a simpler process capable of good yield.

It is a further object to develop new compounds for neutron capture therapy.

These and other objects of the present invention will become apparent from the following description.

The present invention provides a process for the preparation of undecahydrododecaborate anions $[B_{12}H_{(12-n)}(XCN)_n]^{2-}$ or $[B_{12}H_{11}XH]^{2-}$ or nonahydrodecaborate anions formula $[B_{10}H_{(10-n)}(XCN)_n]^{2-}$ or $[B_{10}H_9XH]^{2-}$ where X=O, S or Se; and n=1, 2 or 3; which comprises the reaction of a dodecahydrododecaborate anion $[B_{12}H_{12}]^{2-}$ or decahydro decaborate anion $[B_{10}H_{10}]^{2-}$ with a compound $A^+NCX^-$ where $A^+$=an alkali metal cation selected from Li, Na, K or Cs;

an alkaline earth metal cation selected from ½Ca, ½Mg; $[R_4P]^+$, $[R_3HP]^+$, $[R_4N]^+$, $[R_3HN]^+$;

where R is a $C_{1-20}$ alkyl, aryl, or $C_{1-20}$ alkyl substituted aryl group;

the reaction being either an electrochemical oxidation reaction, or the reaction being conducted in the presence of an oxidising agent.

In order to ensure complete reaction, the amount of electrical charge supplied in the electrochemical or chemical oxidation will generally be sufficient to bring about the one-electron oxidation of the NCX ion to generate the radical NCX. Without wishing to be limited by any speculated mechanism, it is believed that this radical subsequently reacts with $[B_{12}H_{12}]^{2-}$ as follows:

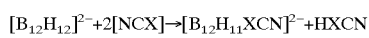

$$[B_{12}H_{12}]^{2-}+2[NCX] \rightarrow [B_{12}H_{11}XCN]^{2-}+HXCN$$

so that in general the reaction may be viewed as representing a two electron process. In the case of chemical oxidation, the oxidant may be hydrogen peroxide, benzoyl peroxide, cupric ion, ceric ion, chromate or dichromate ion, or halogen e.g. Cl, Br, F, or I. The oxidant is preferably used in acid solution.

Generally, the $[B_{12}H_{12}]^{2-}$ anion used as starting material will be in the form of the compound $[Et_3NH]_2 [B_{12}H_{12}]$. However, other analogous starting materials may also be used, including $[R_4N]_2 [B_{12}H_{12}]$ (where R is preferably methyl, ethyl, propyl or butyl) or $(W)_2 [B_{12}H_{12}]$ wherein W represents Cs, K, Na or Li.

The reaction set out above generally gives rise to the compound $A_2[B_{12}H_{11}XCN]^{2-}$ or $A_2[B_{10}H_9XCN]^{2-}$ respectively. Further reaction with additional [NCX] produces multiple substituted anions for example, $[B_{12}H_{10}(XCN)_2]^{2-}$ or $[B_{10}H_8(XCN)_2]^{2-}$. These intermediates may then be reduced for example using sodium in liquid $NH_3$ to give the corresponding salts for example $A_2 [B_{12}H_{11}XH]$ or $A_2 [B_{10}H_9XH]$.

In order that the intermediate compounds are more easily separated from the reaction mixture, it is preferred that the cation A shall be a bulky cation, such as the ammonium and phosphonium cations mentioned above. Preferably, R is a $C_{1-8}$ alkyl group. Preferred aryl groups include phenyl, tolyl and naphthyl groups.

The electrochemical reaction is usually carried out in the solution phase employing a solvent of high conductivity and high dielectric constant. So as not to be decomposed during the electrochemical reaction, the solvent must have a good oxidation/reduction range. Ideally, the solvent should be volatile enough for easy removal under vacuum. Preferred solvents include acetonitrile, dimethylsulphoxide, dimethylformamide, nitromethane, and water.

In a further aspect of the invention there is provided a process for the preparation of an undecahydrododecaborate anion of the formula

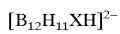

$[B_{12}H_{11}XH]^{2-}$ wherein X is S or Se;
which comprises (i) the reaction of a dodecahydrododecaborate anion $[B_{12}H_{12}]^{2-}$ with a compound $X=C(NR^1R^2)_2$ wherein $R_1$ and $R^2$ are the same or different and are selected from H and $C_1$–$C_6$ alkyl; the reaction being either an electrochemical oxidation reaction or the reaction being conducted in the presence of an oxidising agent and resulting in the formation of a urea derivative of the formula $[B_{12}H_{11}XC(NR^1R^2)_2]^-$; and (ii) the hydrolysis of said urea derivative under alkaline conditions.

In a preferment, the urea derivative is a thiourea derivative wherein X is S and $R^1$ and $R^2$ are both H.

The preparation of $[B_{12}H_{11}XH]^{2-}$, when produced by way of electrochemical oxidation is typically carried out in an electrochemical cell with anode and cathode compartments being separated by a semi-permeable anion exchange membrane. Generally, a suitable supporting electrolyte, such as $CF_3SO_3NBu_4$ in acetonitrile, is required. In stage 1 of the process, in the presence of a suitable supporting electrolyte the following reaction takes place:

$[B_{12}H_{12}]^{2-}+X=C(NR^1R^2)_2 \rightarrow [B_{12}H_{11}XC(NR^1R^2)_2]^- + H^+$ The reaction product may be transferred into an acid such as $H_3O^+[B_{12}H_{11}XC(NR^1R^2)_2]^-$ by passing the reaction mixture through a column made up of a suitable resin, such as Dowex 50 resin in H-form and purified by recrystallisation of an alkali metal salt of the anion, for example, the cesium salt from water and ethanol mix, in a suitable ratio, for example a ratio of 3 parts ethanol: 1 part water.

The alkali metal salt of the $[B_{12}H_{11}XC(NR^1R^2)_2]^-$ anion is then subjected to hydrolysis under suitable alkaline conditions, e.g. 1M NaOH for 10 minutes at up to 80° C. or may be subjected to reflux conditions, for example for about 1 hour in 10% $NH_4OH$: $[B_{12}H_{11}XC(NR^1R^2)_2]^-+OH^-(NH_3) \rightarrow [B_{12}H_{11}XH]^{2-}+(R^2R^1N)_2CO[(H_2N)_3C]^+$ In a further aspect of the present invention, intermediate cations are provided which are formed during the electrochemical oxidation reaction or the reaction conducted in the presence of an oxidising agent, of the following formula:

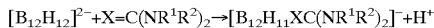

$[\{(R^1R^2N)_2CX\}_2]^{2+}$ wherein $R^1$ and $R^2$ are the same or different and are selected from H and $C_1$–$C_6$ alkyl; and X is S or Se.

The reaction with $NH_3$ may be used as a basis for the preparation of substantially pure BSH. For example, after ammonolysis, the reaction mixture can be evaporated to dryness and the residue, comprised of suitable cations such as alkali metal ions and the like, for example, $Cs^+$ and guanidinium ion can be dissolved in water and passed through a suitable cation exchange column, comprising, for example, a Dowex 50 resin in H-form. The eluate can then be neutralised with alkali, for example, NaOH, to a suitable pH, for example pH 5–6, filtered and dispensed into containers prior to storage. Generally, all of the above reactions are carried out under non-oxidative conditions such as in a nitrogen gas atmosphere or the like.

For reasons of convenience, it is preferred if X is S and $R^1$ and $R^2$ are both H.

The selenium compounds and thiourea derivatives of the present invention are novel. Therefore, another aspect of the present invention provides novel anions of the formulae $[B_{12}H_{11}(SCN)_2]^{2-}$, $[B_{10}H_9SeH]^{2-}$, $[B_{12}H_{11}SeH]^{2-}$, $[B_{10}H_9SeCN]^{2-}$, $[B_{12}H_{11}SeCN]^{2-}$, $[B_{12}H_{10}(SeCN)_2]^{2-}$, $[B_{12}H_{11}SC(NR^1R^2)_2]^-$ and $[B_{12}H_{11}SeC(NR^1R^2)_2]^-$ wherein $R^1$ and $R^2$ are the same or different and are selected from $C_1$–$C_6$ alkyl and H.

A further aspect of the invention provides sulphur and selenium compounds together with a pharmaceutical carrier for use in medical therapy, particularly BNCT. Thus, there is provided use of a sulphur or selenium containing compound selected from $[B_{10}H_9SeH]^{2-}$, $[B_{12}H_{11}SeH]^{2-}$, $[B_{10}H_9SeCN]^{2-}$, $[B_{12}H_{11}SeCN]^{2-}$, $[B_{10}H_9SCN]^{2-}$, $[B_{12}H_{11}SCN]^{2-}$, $[B_{12}H_{10}(SCN)_2]^{2-}$, $[B_{12}H_{11}SC(NR^1R^2)_2]^-$ and $[B_{12}H_{11}SeC(NR^1R^2)_2]^-$ wherein $R^1$ and $R^2$ are the same or different and are selected from $C_1$–$C_6$ alkyl and H together with a pharmaceutical carrier in the manufacture of a medicament for the treatment of cancer.

Examples and Figures illustrating the present invention follow. It is to be understood that the examples are not to be construed as limiting the scope of the invention in any way.

EXAMPLE 1 (X=O)

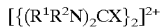

Figure 1:
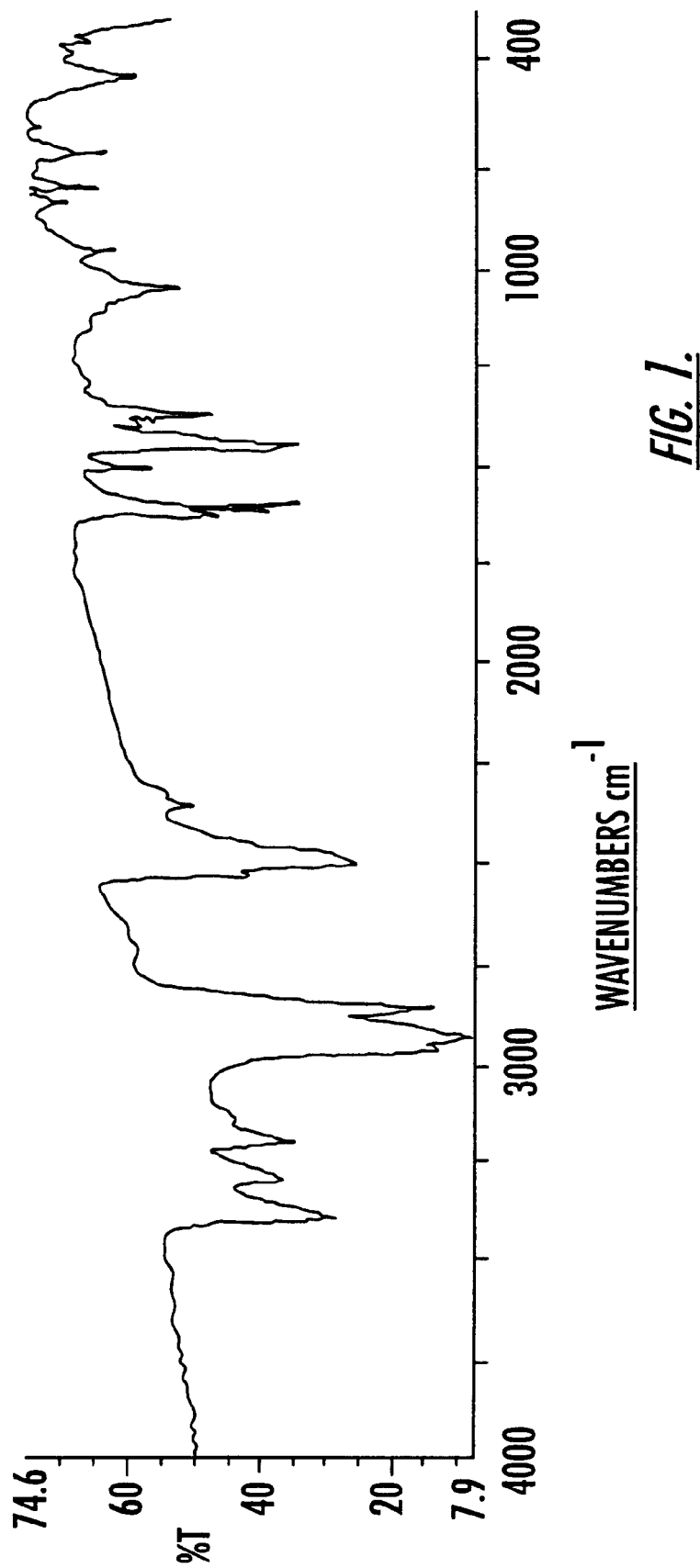
FIG. 1: IR spectrum of Cs $[B_{12}H_{11}SC(NH_2)_2]$ in nujol.
Figure 2A:
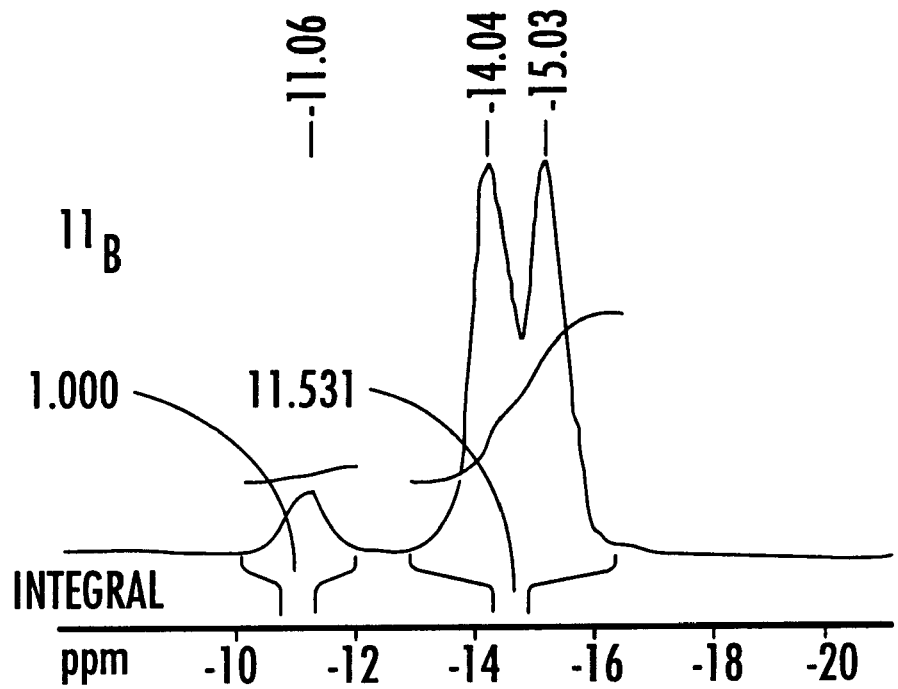
FIG. 2: $^{11}B$ NMR spectra (Rel. $Et_2OBF_3$) of (a,b) $[B_{12}H_{11}SC(NH_2)_2]^-$ and (c,d) $[B_{12}H_{11}SH]^{2-}$ from its alkaline hydrolysis.
Figure 2B:
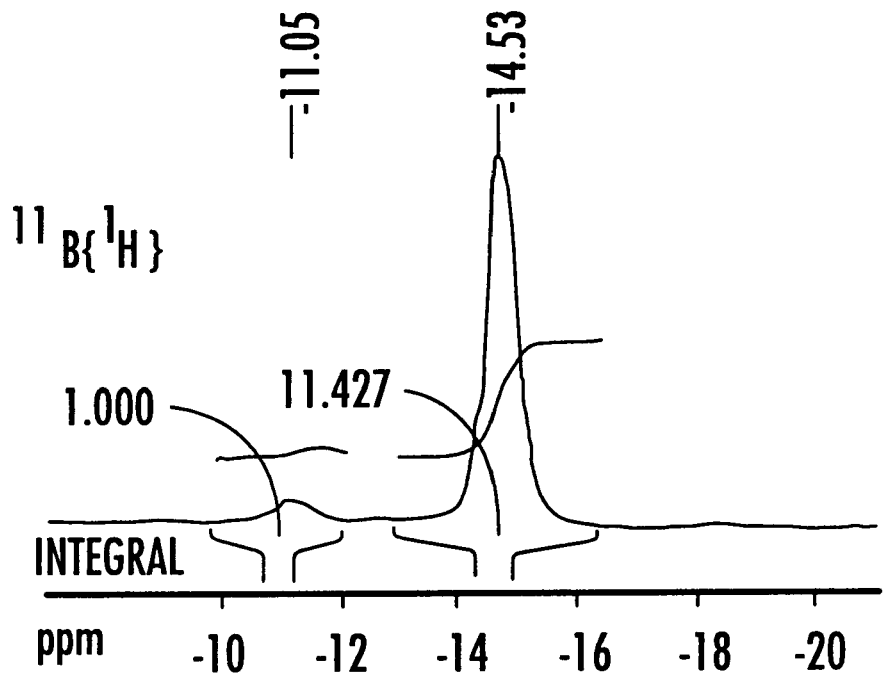
Figure 2C:
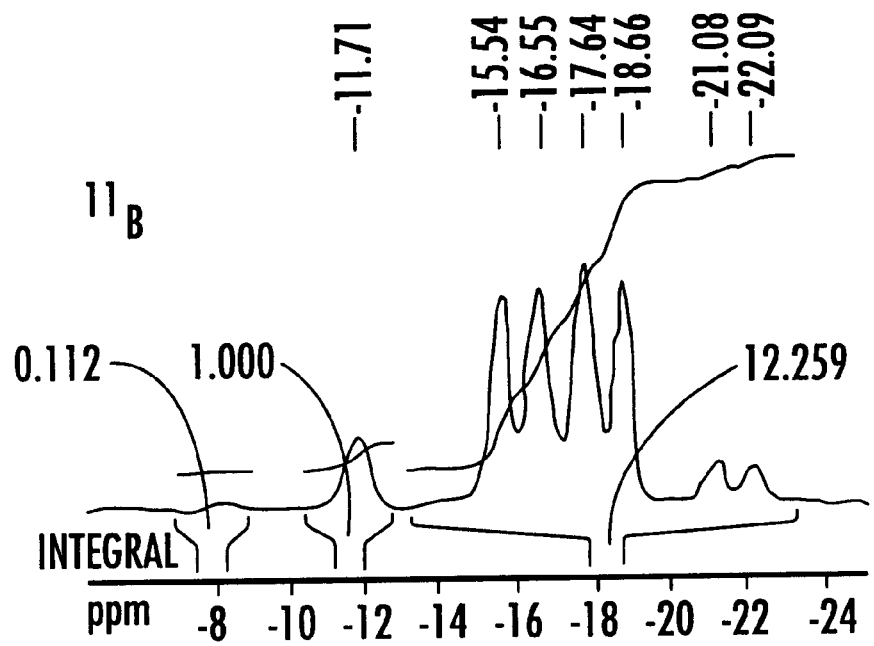
Figure 2D:
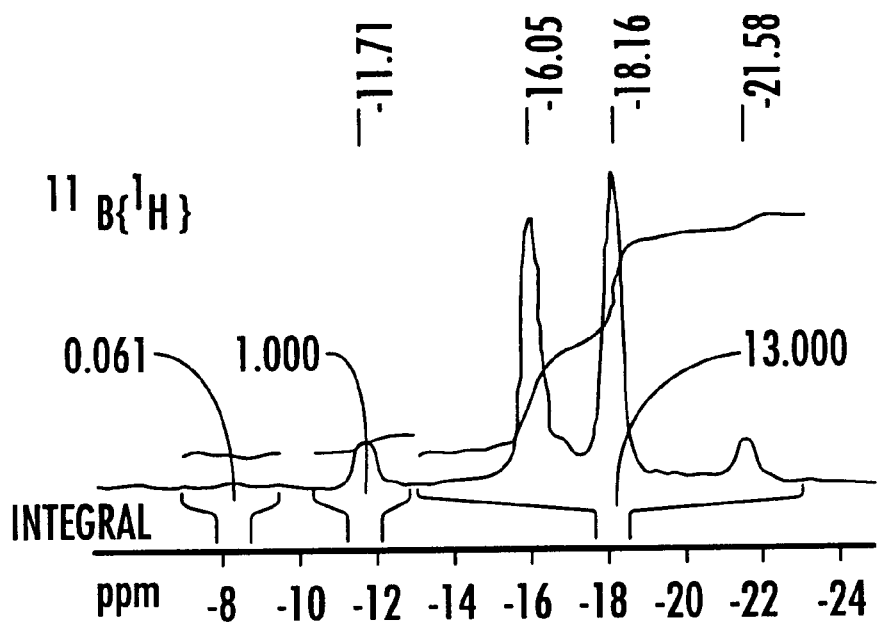

An electrochemical cell was set up, of two U-shaped compartments, where the anodic and cathodic compartments were separated by NAFION ion exchange membrane. The working electrode consisted of platinum gauze, the auxiliary electrode of platinum foil, and the reference electrode was a silver wire.

An EG and G Princeton Applied Research potentiostat-.galvanostat was used with a limiting current of 100 mA and a potential of 0.8V. Acetonitrile was purified by the method used by Winfield and co-workers (J. M. Winfield, J. Fluorine. Chem., 1984, 25, 91).

$[C_2H_5)_3NH]_2[B_{12}H_{12}]$ (Boron Biologicals Ltd, U.S.A.) (0.49 g, 2 mmol) and $[(Ph_3P)_2N][NCO]$ (Aldrich Chemical) (2.32 g, 4 mmol) in acetonitrile (40 ml) were added to the anodic compartment of the cell. The cathodic compartment contained $[(Ph_3P)_2N][NCO]$ (1.16 g. 2 mmol) as conducting electrolyte for the reaction in acetonitrile solvent (15 ml).

After 386 Coulombs (4 mmol) of charge had passed, the reaction was stopped. At this stage the solution was taken up to dryness to produce a gum. The gum was taken up in warm 28% aqueous ethanol and left to cool to produce white crystals of [(Ph$_3$P)$_2$N]$_2$[B$_{12}$H$_{11}$OCN] (0.617 g, 0.5 mmol), 24% yield. The compound was identified by $^{11}$B and $^1$H nmr studies.

EXAMPLE 2 (X=S)

(A) Preparation of [Ph$_3$P)$_2$N] [SCN]

[(Ph$_3$P)$_2$N] [Cl] (Aldrich Chemical) (11.47 g, 20 mmol) was dissolved in warm water and to this was added a solution of [NH$_4$] [NCS] (1.52 g, 20 mmol) in as little water as possible. A white precipitate appeared immediately and the solution was filtered. Recrystallisation was carried out using CH$_2$Cl$_2$/Et$_2$O solvent to produce [(Ph$_3$P)$_2$N] [SCN] (10.73 g, 18 mmol).

The infra-red spectrum indicates the NCS stretching mode at 2,120 cm$^{-1}$.

Found: C, 47.0; N, 4.67; S, 5.31; H, 5.0%. [(Ph$_3$P)$_2$N] [NCS] requires: C, 74.50; N, 4.70; S, 5.37; H, 5.03%.

(B) Electrochemical Preparation of [(Ph$_3$P)$_2$N]$_2$ [B$_{12}$H$_{11}$SCN]

[(C$_2$H$_5$)$_3$NH]$_2$[B$_{12}$H$_{12}$] (0.49 g, 2 mmol) and [(Ph$_3$P)$_2$N] [SCN] (2.38 g, 4 mmol) in acetonitrile solvent (40 ml) were placed in the anodic compartment of the cell. The cathodic compartment contained [(Ph$_3$P)$_2$N] [SCN] (1.19 g, 2 mmol) as conducting electrolyte for the reaction in acetonitrile solvent (15 ml).

After 386 Coulombs (4 mmol) of charge had passed, and the solution became more intensely yellow in colour the reaction was stopped. At this stage the solution was taken to dryness under vacuum to produce yellowish gum. The gum was taken up in warm 20% aqueous ethanol and left to cool to produce white crystals of [(Ph$_3$P)$_2$N]$_2$[B$_{12}$H$_{11}$SCN] (1.87 g, 1.5 mmol, 73% yield) as indicated by $^{11}$B and $^1$H nmr studies.

EXAMPLE 3 (X=S)

(A) Preparation of [C$_2$H$_5$)$_3$NH] [SCN]

A solution of [NH$_4$] [SCN] (Aldrich Chemicals) (7.6 g, 0.1 mmol) in acetonitrile (80 cm$^3$) was added to a solution of (C$_2$H$_5$)$_3$N (14 cm$^3$, 1 mmol) in acetonitrile (40 cm$^3$) and acetic acid (6 cm$^3$, 0.11 mmol). Immediately a white crystalline product precipitated, which was filtered off, washed several times with acetonitrile, and dried in vacuo to yield a constant weight of 13.5 g. (84%) of pure [(C$_2$H$_5$)$_3$NH] [SCN]. Since the compound is very hygroscopic, it is stored in a tightly closed vessel.

(B) Electrochemical Preparation of Cs$_2$[B$_{12}$H$_{11}$SCN]

A similar preparation was carried out (as previously) using [(C$_2$H$_5$)$_3$NH] [SCN] (0.32 g, 2 mmol) in the place of [(Ph$_3$P)$_2$N] [SCN].

After evaporation to dryness under vacuum, a yellow/orange gum produced. CsOH (0.3 g, 10–20% water content) was dissolved in as little water as possible and to this was added the yellow gum. Triethylamine vapour was given off to produce white crystals of Cs$_2$[B$_{12}$H$_{11}$SCN] (0.66 g, 1.5 mmol, 73% yield) which were filtered and washed with ethanol.

EXAMPLE 4 (X=S)

Preparation of Tetraethylammonium S-(thiocyano)-closo-dodecaborate [(C$_2$H$_5$)$_4$N]$_2$[B$_{12}$H$_{11}$SCN]

To the suspension of 9.30 g (26.9 mmol) [(C$_2$H$_5$)$_3$NH)]$_2$, [B$_{12}$H$_{12}$] in 50 ml of water there was added 15 ml (75 mmol) of 5M NaOH and the mixture was partially evaporated in vacuo till complete dissolution of the precipitate. The resulting solution of Na$_2$[B$_{12}$H$_{12}$] was adjusted to 50 ml volume with water and cooled with ice water. 30 ml of concentrated H$_2$SO$_4$ was added to 30 ml of water under ice cooling and to the cooled solution there was added 50 ml (100 mmol) of 2M H$_2$O$_2$. The prepared solution was poured into the solution of Na$_2$[B$_{12}$H$_{12}$].

Under mechanical stirring and ice cooling 6.3 g (53.6 mmol) of NaSCN.2H$_2$O in 12 ml of water were added and stirring continued until complete disappearance of the purple colour of the reaction mixture. To the clear solution of the reaction mixture a solution of 13.00 g (59.9 mmol) [(C$_2$H$_5$)$_4$N] [BF$_4$] in 30 ml H$_2$O was added. A white crystalline precipitate was formed which was filtered off, washed with water (3×30 ml) and recrystallised twice from hot water yielding 10.47 g (83.3%) of [(C$_2$H$_5$)$_4$N]$_2$ [B$_{12}$H$_{11}$SCN].

The $^{11}$B NMR spectrum of the prepared compound consists of a singlet intensity 1 at –9.7 ppm and 3 doublets at –14.4, –14.9 and –16.8 ppm of relative intensities 5:5:1 indicating a monosubstituted closo-B$_{12}$ derivatives.

IR spectrum of the compound measured in nujol H mull contains a sharp band at 2138 cm$^{-1}$ indicating the presence of a CN group and a broad band of B—H vibrations at 2600–2800 cm$^{-1}$.

EXAMPLE 5 (X=S)

Electrochemical Thiocyanation of [(C$_2$H$_5$)$_3$NH]$_2$ [B$_{12}$H$_{12}$]

The anode cell of the electrochemical unit was loaded with 1.00 g (2.89 mmol) of [(C$_2$H$_5$)$_3$NH]$_2$ [B$_{12}$H$_{12}$] 0.62 g (8.15 mmol) of NH$_4$SCN and 40.0 ml of CH$_3$CN. Into the cathode cell 0.30 g (3.95 mmol) NH$_4$SCN and 15.0 ml CH$_3$CN were placed. The potential in the anode cell was adjusted to +1.00V and electrolysis started. Evolution of H$_2$ was observed at the cathode. Under stirring the precipitate of [(C$_{12}$H$_5$)$_3$NH]$_2$[B$_{12}$H$_{12}$] was slowly dissolved and the temperature increased to 38–40° C. The reaction was continued till the consumption of 600 Coulombs (107.5%, calculated to the mono-substituted product) and then stopped. To the reaction mixture 40 ml of water and 2.0 ml 5M NaOH were added and the solution was evaporated in vacuo to dryness. The solid residue was dissolved in 15 ml of water and 1 ml of acetic acid. The solution was filtered and precipitated with 5 ml 2M [(C$_2$H$_5$)$_4$N] Br. The precipitate formed was filtered off and recrystallised from hot water. After drying in air 1.04 g (75.5%) of [(C$_2$H$_5$)$_4$N]$_2$[B$_{12}$H$_{11}$SCN] were obtained.

IR spectrum of the sample of the prepared compound in nujol showed an intense absorption band of CN stretching vibrations at 2138 cm$^{-1}$ and a broad band of B—H vibrations at 2600–2800 cm$^{-1}$.

$^{11}$B NMR spectrum of the sample consists of 4 resonance frequencies at –9.7, –14.9 and –16.8 ppm of relative intensities of 1:5:5:1. The resonance band at –9.7 ppm is a singlet in the $^{11}$B proton nondecoupled spectrum indicating monosubstituted closo-B$_{12}$ moiety.

EXAMPLE 6 (X=Se)

Electrochemical Preparation of Cs$_2$[B$_{12}$H$_{11}$SeCN]

[C$_2$H$_5$)$_3$NH]$_2$[B$_{12}$H$_{12}$] (0.49 g, 2 mmol) and KSeCN (0.58 g, 4 mmol) in acetonitrile solvent (40 ml) was placed in the anodic compartment of the cell. The cathodic compartment contained KSeCN (0.29 g, 2 mmol) as conducting electrolyte for the reaction in acetonitrile solvent (15 ml).

After 400 Coulombs (4.1 mmol) of charge had passed, the solution became intense red in colour, and the reaction was stopped.

The solution was taken to dryness to produce a red gum. CsOH (0.8 g, 10–20% water content) was dissolved in as little water as possible and the red gum was added to this to produce crystals which were filtered and washed with 20% aqueous ethanol to give $Cs_2[B_{12}H_{11}SeCN]$ (0.73 g, 1.5 mmol, 72% yield) indicated by $^{11}B$ and $^{1}B$ nmr studies.

Resonances were observed at −11.65, −13.95, −15.10, −17.05 ppm of relative intensities 1:5:5:1 from the $^{11}B\ \{^{1}H\}$ spectrum.

The $^{11}B$ spectrum contains a singlet at −11.65 ppm representing the SeCN containing boron atom.

EXAMPLE 7

Preparation of $Na_2[B_{12}H_{11}SH]$

Reduction of $[(C_2H_5)_4N]_2[B_{12}H_{11}SCN]$ (Example 5) with sodium in liquid $NH_3$ was carried out as follows. To 2.52 g (5.5 mmol) of $[(C_2H_5)_4N]_2[B_{12}H_{11}SCN]$ placed in a 100 ml round bottomed flask 70 ml of dry liquid ammonia was added and a clear solution was formed. 0.8 g of sodium metal was added in small pieces to this solution, waiting each time for the complete disappearance of the blue colour. Addition of sodium was continued until the appearance of persistent blue colour. The ammonia was allowed to evaporate and the rest of volatile products was completely removed in vacuo. The flask containing a dry solid was filled with dry nitrogen, and then there were successively added 10 ml of ethanol, 15 ml of glacial acetic acid and 2 ml of thioglycolic acid. The mixture was heated to 80° C. for 5–10 minutes for complete dissolution of the solid, the hot solution filtered, 30 ml of diethyl ether was added and the mixture left for 20–30 minutes at room temperature to crystallise.

A white precipitate was formed which was filtered off, washed with acetic acid and dried in vacuo, yielding 1.04 g (86%) of $Na_2[B_{12}H_{11}SH]$. After recrystallisation from acetic acid under nitrogen there was obtained 0.92 g (76%) of $Na_2[B_{12}H_{11}SH]$ which was characterised by its $^{11}B$ NMR spectrum. The sample of $Na_2[B_{12}H_{11}SH]$ contained as impurity 1.7% of $Na_2[B_{12}H_{12}]$.

EXAMPLE 8

Preparation of $Na_2[B_{12}H_{11}SCN]$ from $[(C_2H_5)_4N]_2[B_{12}H_{11}SCN]$ $[(C_2H_5)_4N]_2[B_{12}H_{11}SCN]$ (3.30 g, 7.2 mmol) was dissolved in a mixture of $CH_3CN$ (6 cm$^3$), $H_2O$ (6 cm$^3$), and $CH_3OH$ (3 cm$^3$) and the solution was passed through a column filled with 15 cm$^3$ of cationite Dowex 50 in its H$^+$ form which had been previously washed with a similar mixture of solvents. An acid fraction was collected and titrated with NaOH to pH 7.0 and required exactly 14.4 mmol for neutralisation. The clear solution was evaporated to complete dryness on a rotary evaporator yielding 1.80 g of $Na_2[B_{12}H_{11}SCN]$. The i.r. spectrum of the compound showed a sharp band of 2138 cm$^{-1}$ due to the C≡N group, and a broad band at 2600–2800 cm$^{-1}$ due to B—H stretching vibrations.

The compound is very soluble in water, and this enhances its application in biological trials in animal models.

EXAMPLE 9

Preparation of $Na_2[B_{12}H_{10}(SCN)_2]$ from $[(C_2H_5)_4N]_2[B_{12}H_{10}(SCN)_2]$ A solution of $[(C_2H_5)_4N]_2[B_{12}H_{10}(SCN)_2]$ (Example 11) (1.80 g, 3.5 mmol) in a mixture of $CH_3CN: H_2O: CH_3OH$ (2:2:1) was passed through a cationite Dowex 50 in its H$^+$ form, neutralised with NaOH, and evaporated to dryness to yield 1.1 g of $Na_2[B_{12}H_{10}(SCN)_2]$. The compound, which was freely soluble in water, showed a strong sharp i.r. band at 2140 cm$^{-1}$ due to the C≡N groups.

EXAMPLE 10

Electrochemical Thiocyanation of $[B_{12}H_{12}]^{2-}$ in Aqueous Acid Solution

To the anode compartment of the electrochemical cell were placed sequentially 6 cm$^3$ of 0.5M $Na_2[B_{12}H_{12}]$ (3.0 mmol), 2 cm$^3$ of 5.0M NaSCN (10 mmol), 24 cm$^3$ of water and 8 cm$^3$ of $H_2SO_4$ (1:1 v/v). In the cathode compartment were placed 1 cm$^3$ of 5.0 M NaSCN, 11 cm$^3$ of water and 3 cm$^3$ of $H_2SO_4$ (1:1 v/v). The cell was cooled in ice and the electrochemical process started at a potential of 0.6V (I˜300 mA). After passing 580 Coulombs, the reaction was stopped and the clear solution was treated with 15 cm$^3$ of 0.5M $[(C_2H_5)_4N][BF_4]$ (7.5 mmol). The white precipitate was filtered off, washed with water, and dried in air yielding 1.25 g (90.7%) of $[(C_2H_5)_4N]_2[B_{12}H_{11}SCN]$ of approximately 95% purity (by $^{11}B$ NMR integral measurements).

EXAMPLE 11

Preparation of $[(C_2H_5)_4N]_2[B_{12}H_{10}(SCN)_2]$ using $K_2Cr_2O_7$ as an oxidizer To a solution of $[(C_2H_5)_4N]_2[B_{12}H_{12}]$ (9.47 g, 23.55 mmol) $\{[(C_2H_5)_4N]_2[B_{12}H_{12}]$ can be prepared from a soluble salt such as $Na_2[B_{12}H_{12}]$ or $[(C_2H_5)_3NH]_2[B_{12}H_{12}]$ by metathesis with $[(C_2H_5)_4N]OH$ or $[(C_2H_5)_4N]Cl$ or $[(C_2H_5)_4N]BF_4$ in a molar ratio 1:2 in aqueous solution by a method similar to that of Example 4$\}$.

To a suspension of $[(C_2H_5)_3NH]_2[B_{12}H_{12}]$ (9.3 g, 26.9 mmol) in 50 cm$^3$ of water added 15 cm$^3$ of 5M NaOH and the mixture partially evaporated in vacuo until complete dissolution had occurred. To this clear solution, adjusted to 50 cm$^3$ with water and cooled in ice, was added a solution of $[(C_2H_5)_4N]BF_4$ (13.0 g, 59.9 mmol) in 30 cm$^3$ water, and the white precipitate filtered off, washed with water, and recrystallised from hot water. To a solution of $[(C_2H_5)_4N]_2[B_{12}H_{12}]$ (9.47 g, 23.55 mmol) in a mixture of 200 cm$^3$ of acetonitrile, 50 cm$^3$ of water, and 40 cm$^3$ of $H_2SO_4$ (1:1 v/v) cooled to 5–7° C. was added a solution of $NaSCN.2H_2O$ (12.8 g, 109 mmol) in 20 cm$^3$ of water. A solution of $K_2Cr_2O_7$ (4.85 g, 16.5 mmol) in 30 cm$^3$ of water and 30 cm$^3$ of $H_2SO_4$ (1:1 v/v) was added dropwise with stirring giving a slight evolution of heat (temp.=12° C.). The reaction mixture was stirred for 0.5 hours and concentrated on a rotary evaporator to strip the $CH_3CN$. The residue was refluxed with 1000 cm$^3$ of water and the dark solution filtered. On cooling the product separated first as an oil which solidified into a crystalline mass on standing. The crystalline precipitate was filtered off, washed with water, and dried in air, yielding crude $[(C_2H_5)_4N]_2[B_{12}H_{10}(SCN)_2]$ (10.2 g, 83%). The product was recrystallised from a mixture of 100 cm$^3$ of MeOH and 200 cm$^3$ of water. The $^{11}B$ NMR spectrum showed it to be almost pure 1,7-isomer of $[(C_2H_5)_4N]_2[B_{12}H_{10}(SCN)_2]$. The IR spectrum displayed two intense absorption bands, at 2140 cm$^{-1}$ (due to C≡N str.) and at 2600–2800 cm$^{-1}$ (due to B—H str.).

EXAMPLE 12

Electrochemical Synthesis of $[B_{12}H_{11}SC(NH_2)_2]^-$ Salts 1.012 g (2.92 mmol) of $[(C_2H_5)_3NH)]_2B_{12}H_{12}$, 0.520 g (6.84 mmol) of thiourea and 0.812 g (2.07 mmol) of $[Bu_4N]$

[O$_3$SCF$_3$] (Aldrich Chemical) were placed into the anode compartment of an electrochemical cell and dissolved in 50 ml of CH$_3$CN. 0.408 g (1.02 mmol) of [Bu$_4$N] [O$_3$SCF$_3$] were placed into the cathode compartment of the cell, dissolved in 15 ml of CH$_3$CN, and the reaction started at E=+2.2 V (I=−18 mA) and during the reaction the potential was increased to E=+2.5 V (I=−120 mA). The reaction was carried out until gaining 580 coulombs (103%), and then the current switched off. The slightly yellow solution from the anode compartment was diluted with 50 ml of water and passed through a column, containing 15 g of a cationite Dowex 50 in H-form in CH$_3$CN: H$_2$O 1:1. The acidic fraction was collected, neutralized with 5M NaOH to pH 7.5 and the solvent evaporated to dryness in vacuo. The solid residue was dissolved in 10 ml of water, the solution filtered and treated with 0.56 g (1.70 mmol) of Cs$_2$CO$_3$. A white crystalline product was filtered off, washed with water and dried in air, yielding 655 mg (64.3%) of Cs[B$_{12}$H$_{11}$SC(NH$_2$)$_2$], which was recrystallised twice from water.

By precipitating the diluted aqueous solutions of the cesium salt with Et$_4$NBr and Bu$_4$NBr respectively the corresponding tetraalkylammonium salts were prepared. Et$_4$N[B$_{12}$H$_{11}$SC(NH$_2$)$_2$] found: C 31.00, 30.80; H 10.57, 10.41; B 37.03, 36.87; N 12.70, 12.72; S 8.29, 8.32; C$_9$H$_{35}$B$_{12}$N$_3$S calc: C 31.14; H 10.16; B 37.37; N 12.10; S 9.23. For Bu$_4$N[B$_{12}$H$_{11}$SC(NH$_2$)$_2$] found: C 45.24, 45.24; H 11.61, 11.42; B 27.89, 28.16; N 9.13, 9.30; S 5.49, 5.65. C$_{17}$H$_{51}$B$_{12}$N$_3$S calc: C 44.45; H 11.19; B 28.23; N 9.15; S 6.98.

IR, $^1$H and $^{11}$B NMR spectra of the prepared salts showed unequivocally that the new derivative of [B$_{12}$H$_{12}$]$^{2-}$ represents monosubstituted thiourea derivative [B$_{12}$H$_{11}$SC(NH$_2$)$_2$]$^-$ (FIGS. 1 and 2).

EXAMPLE 13

Chemical Preparation of Cs[B$_{12}$H$_{11}$SC(NH$_2$)$_2$]

To a solution of 11.0 g (50 mmol) of K$_2$B$_{12}$H$_{12}$ (prepared from [(C$_2$H$_5$)$_3$NH]$_2$B$_{12}$H$_{12}$ by treating with KOH) and by 8.0 g (105 mmol) of thiourea in 150 ml of 5% H$_2$SO$_4$ a solution of 5.9 g (20 mmol) of K$_2$Cr$_2$O$_7$ in 100 ml of 5% H$_2$SO$_4$ was added dropwise at room temperature under mechanical stirring. The reaction mixture was stirred for 1 hour. A solution of 14.0 g (85 mmol) of CsCl in 30 ml water was then added to the reaction mixture and the suspension formed was cooled down to 2–4° C. A crystalline precipitate of Cs[B$_{12}$H$_{11}$SC(NH$_2$)$_2$] was filtered off, washed twice in 10 ml aliquots of iced water and re-crystallised twice from ethanol-water (3 parts ethanol: 1 part water). The product was then dried in air. IR spectra for Cs[B$_{12}$H$_{11}$SC(NH$_2$)$_2$] is shown in FIG. 1.

EXAMPLE 14

Preparation of Cs$_2$[B$_{12}$H$_{11}$SH]

To the solution of 0.70 g (2.00 mmol) of Cs[B$_{12}$H$_{11}$SC (NH$_2$)$_2$] in 10 ml of hot water 2 ml (10 mmol) of 5 M NaOH were added together with 20 mg of NaBH$_4$ (to prevent SH oxidation). The solution was heated to 90° C. and kept at this temperature for 15 minutes. To the hot solution, 0.46 g (1.4 mmol) of Cs$_2$CO$_3$ and 0.2 ml of acetic acid were added and the solution was cooled with ice water. The crystalline precipitate of Cs$_2$[B$_{12}$H$_{11}$SH] formed was filtered off, washed with the deoxygenated water and dried in vacuo. According to $^{11}$B NMR spectrum the sample contained about 5% of the disulfide, [Cs$_2$B$_{12}$H$_{11}$S]$_2$ (FIG. 2).

EXAMPLE 15

Preparation of Na$_2$[B$_{12}$H$_{11}$SH]

A solution of 0.5 g (1.14 mmol) of Cs$_2$[B$_{12}$H$_{11}$SH] in 5.0 ml of hot deoxygenated water was passed through a column containing 4 g of a cation exchange resin, Dowex 50 in H-form. The acidic solution was collected and neutralised with 5M NaOH. A solution of Na$_2$[B$_{12}$H$_{11}$SH] was obtained.

EXAMPLE 16

Biological Studies on Na$_2$[B$_{12}$H$_{11}$(SCN)]

1. Toxicity Method

The toxicity of Na$_2$[B$_{12}$H$_{11}$(SCN)] was studied in C57BL/6 male mice (Russican Cancer Research Centre, Moscow) of 19–22 grams in weight: An aqueous solution was injected intraperitoneally in a volume equivalent to ⅟₁₀₀ of each animal's body weight. LD$_{50}$, LD$_{100}$ and LD$_0$ were obtained for 5 groups (6 mice per group), by the method of Karber (in: M L Belenky "The elements of quantitive estimation of pharmacological effect", Ed. Med. Lit., L-d, 1963, p. 49. (Rus.)). The following doses were used:

270.0 236.25 202.5 135.0 67.5 µg. boron per gram. of body weight.

2. Toxicity Results

There were no visible behaviour violations observed in the animals after intraperitoneal injection with the compound. Death at lethal doses did not occur in less than one day. Surviving animals did not show symptoms of chronic intoxication. The values for Na$_2$[B$_{12}$H$_{11}$(SCN)] were: LD$_{100}$>270.0; LD$_{50}$, 236.25; LD$_0$, 135.0 µg.g$^{-1}$.

3. Biodistribution Method

The biodistribution of Na$_2$[B$_{12}$H$_{11}$(SCN)] was studied in C57BL/6 mice (20–23 g) bearing the s.c. B-16 melanoma (Russian Cancer Research Centre, Moscow). The compound was dissolved in distilled water and the solution (0.2–0.23 cm$^3$ containing 150 µg. B per g. body weight) was injected interperitoneally into C57BL/6 male mice (20–23 g) 11 days after the hosts were subcutaneously inoculated with B-16 melanoma cells. The animals were decapitated 1, 3, 6, and 24 hours after injection. Since the successful treatment of neoplasms by the BNCT method requires a boron concentration gradient between the tumour and the tissue adjacent to it in the radiated volume (B in tumour/B in adjacent tissue>>1) after sufficient clearance of the blood. Therefore, the tumour and the tissues adjacent to it (skin, tumour bed, muscle) were excised and the boron content determined. In addition, the blood, urine, tissues of excretory organs (liver, kidneys, lung) and the heart and spleen were analysed. The organs were excised, rinsed in pharmacological saline, dried with filter paper, and weighed. They were then dried to constant weight. The boron content was determined by prompt gamma ray activation analysis in the IR-68 reactor at the RRC Kurchatov Institute. The boron content was calculated per gram of crude tissue. The dependence of boron content in tissues (µg.g$^{-1}$) was calculated from the average of 4–6 animals not indicating verified interval.

4. Biodistribution Results

The results of the biodistribution study of Na$_2$[B$_{12}$H$_{11}$ (SCN)] are presented in Tables 1 and 2. The highest boron concentration in the tumour was found 1 hour after injection (48.9 µg/g), although at this time, the skin content was similar (55.0 µg/g). The boron content in the blood 1 hour after injection was 2.5 times that in the tumour. The optimal ratio of boron in tumour to that in adjacent tissues was achieved at 24 hours when the boron content of the tumour was 19.9 µg/g and the boron content of skin, muscles and blood were 1.7, 5.5 and 3.4 times less than that in the tumour respectively.

The compound rapidly eliminated by the liver, kidneys and lung. The elimination curves did not show renal intoxication.

The toxicological and pharmacokinetic characteristics suggest that $Na_2[B_{12}H_{11}(SCN)]$ is a good candidate for the treatment of tumours by BNCT.

TABLE 1

Boron Content of $Na_2[B_{12}H_{11}(SCN)]$ in Tissue ($\mu g \cdot g^{-1}$)

| | Time after Administration of Compound | | | |
|---|---|---|---|---|
| | 1 hour | 2 hours | 6 hours | 24 hours |
| Blood | 120.7 | 10.4 | 8.7 | 5.8 |
| Tumour | 48.9 | 32.0 | 23.0 | 19.9 |
| Skin | 55.0 | 12.7 | 38.8 | 11.7 |
| Muscle | 10.4 | 7.6 | 12.9 | 3.6 |
| Liver | 216.0 | 38.1 | 37.9 | 9.8 |
| Kidneys | 123.3 | 27.1 | 10.5 | 5.2 |
| Lung | 115.8 | 19.5 | 11.8 | 4.5 |
| Heart | 49.6 | 16.1 | 9.5 | 9.9 |

TABLE 2

Ratio of Boron in Tumour to Boron in Tissue for $Na_2[B_{12}H_{11}(SCN)]$

| | Time after Administration of Compound | | | |
|---|---|---|---|---|
| | 1 hour | 2 hours | 6 hours | 24 hours |
| Blood | 0.41 | 3.08 | 2.64 | 3.40 |
| Skin | 0.89 | 2.52 | 0.59 | 1.70 |
| Muscle | 4.70 | 4.23 | 1.78 | 5.50 |
| Liver | 0.23 | 0.84 | 0.61 | 2.02 |
| Kidneys | 0.40 | 1.18 | 2.19 | 3.84 |
| Lung | 0.42 | 1.64 | 1.95 | 4.41 |
| Heart | 0.99 | 1.98 | 2.42 | 2.01 |

What is claimed is:

1. A process for the preparation of undecahydrododecaborate anions $[B_{12}H_{(12-n)}(XCN)_n]^{2-}$ or $[B_{12}H_{11}XH]^{2-}$ or nonahydrodecaborate anions $[B_{10}H_{(10-n)}(XCN)_n]^{2-}$ or $[B_{10}H_9XH]^{2-}$ where X=O, S or Se; and n=1, 2 or 3; said process comprising reacting, under chemical oxidizing conditions, a dodecahydrododecaborate anion $[B_{12}H_{12}]^{2-}$ or decahydro decaborate anion $[B_{10}H_{10}]^{2-}$ with a compound $A^+NCX^-$ where $A^+$=an alkali metal cation selected from $Li^+$, $Na^+$, $K^+$ or $Cs^+$;

an alkaline earth metal cation selected from ½$Ca^+$, ½$Mg^+$; $[R_4P]^+$, $[R_3HP]^+$, $[R_4N]^+$, $[R_3HN]^+$;

where R is a $C_{1-20}$ alkyl, aryl, or $C_{1-20}$ alkyl substituted aryl group.

2. The process according to claim 1 wherein the reaction is conducted in the presence of a chemical oxidizing agent selected from hydrogen peroxide, benzoyl peroxide, cupric ion, ceric ion, chromate ion, dichromate ion or halogen.

3. The process according to claim 1 wherein the $[B_{12}H_{12}]^{2-}$ anion starting material is selected from $[R_4N]_2[B_{12}H_{12}]$, $[R_3NH]_2[B_{12}H_{12}]$, or $(W)_2[B_{12}H_{12}]$ wherein R is selected from methyl, ethyl, propyl or butyl and W represents $Cs^+$, $K^+$, $Na^+$ or $Li^+$.

4. The process according to claim 1 wherein $A^+$ is selected from alkali metal cations selected from $Li^+$, $Na^+$, $K^+$ or $Cs^+$; alkaline earth metal cations selected from ½ $Ca^+$ and ½ $Mg^+$; and $[R_4P]^+$, $[R_3HP]^+$, $[R_4N]^+$ or $[R_3HN]^+$ where R is selected from $C_1$–$C_{20}$ alkyl, aryl or $C_1$–$C_{20}$ alkyl substituted aryl group.

5. The process according to claim 1 wherein R is selected from $C_1$–$C_8$ alkyl, phenyl, tolyl and naphthyl.

6. The process according to claim 1 wherein the $[B_{12}H_{12}]^{2-}$ anion is in the form $[(C_2H_5)_3NH]_2[B_{12}H_{12}]$.

* * * * *